United States Patent
Hamer et al.

(10) Patent No.: US 7,235,251 B2
(45) Date of Patent: Jun. 26, 2007

(54) COSMETIC OR DERMATOLOGICAL OIL/WATER EMULSIONS WITH REDUCED LIPID CONTENT

(75) Inventors: Gunhild Hamer, Hamburg (DE); Kerstin Heike, Hamburg (DE); Waltraud Kaden, Hamburg (DE); Rainer Kropke, Schenefeld (DE); Ghita Lanzendörfer, Hamburg (DE); Gunther Schneider, Hamburg (DE)

(73) Assignee: Beiersdorf AG, Hamburg (DE)

( * ) Notice: Subject to any disclaimer, the term of this patent is extended or adjusted under 35 U.S.C. 154(b) by 687 days.

(21) Appl. No.: 10/648,874

(22) Filed: Aug. 27, 2003

(65) Prior Publication Data
US 2004/0037795 A1 Feb. 26, 2004

Related U.S. Application Data

(63) Continuation of application No. 09/622,090, filed as application No. PCT/EP99/00581 on Jan. 29, 1999, now abandoned.

(30) Foreign Application Priority Data
Feb. 13, 1998 (DE) ................. 198 05 918

(51) Int. Cl.
*A61K 8/00* (2006.01)
*A61K 8/02* (2006.01)
*A61K 8/06* (2006.01)
*A61K 31/715* (2006.01)

(52) U.S. Cl. .................. 424/401; 424/400; 514/54
(58) Field of Classification Search ................ 424/400, 424/401; 514/54
See application file for complete search history.

(56) References Cited

U.S. PATENT DOCUMENTS

| | | | |
|---|---|---|---|
| 4,923,685 A | 5/1990 | Wuelknitz et al. | |
| 5,284,833 A | 2/1994 | McAnalley et al. | 424/543 |
| 5,368,850 A | 11/1994 | Cauwet et al. | |
| 5,494,938 A | 2/1996 | Kawa et al. | |
| 5,585,104 A | 12/1996 | Ha et al. | |
| 5,679,656 A | 10/1997 | Hansenne | 514/54 |
| 5,795,978 A | 8/1998 | Ansmann et al. | |
| 5,958,431 A | 9/1999 | Brancq et al. | 424/401 |

FOREIGN PATENT DOCUMENTS

| | | |
|---|---|---|
| DE | 4040655 | 6/1992 |
| DE | 4103681 | 8/1992 |
| DE | 19542572 | 5/1997 |
| DE | 19543633 | 5/1997 |
| EP | 0 304 627 A2 | 3/1989 |
| FR | 2 698 004 A1 | 5/1994 |
| JP | 62-175145 | 7/1987 |
| JP | 6-172788 | 6/1994 |
| WO | WO 92/06778 | 10/1990 |
| WO | WO 92/07543 | 5/1992 |
| WO | WO 95/13863 | 5/1995 |
| WO | WO 96/32092 | 10/1996 |
| WO | WO 99/40886 | 8/1999 |

OTHER PUBLICATIONS

English language abstract of JP 62-175145.
English language abstract of JP6-172788.
English language abstract of DE 19543633.
English language abstract of DE 4103681.
English language abstract of DE 4040655.

*Primary Examiner*—Shelley A. Dodson
(74) *Attorney, Agent, or Firm*—Greenblum & Bernstein, P.L.C.

(57) ABSTRACT

Cosmetic or dermatological preparations comprising
(I) one or more surface-active substances chosen from the group
  (Ia) of alkyl glucosides
  (Ib) of the disaccharides esterified with one or more fatty acid residues
    (II) one or more surface-active substances chosen from the group
  (IIa) of glycerol esters of saturated or unsaturated fatty acids
  (IIb) of glycol esters of saturated or unsaturated fatty acids
  (IIc) of one or more fatty alcohols chosen from the group of branched and unbranched alkyl alcohols having 12 to 40 carbon atoms
(III) a water phase
(IV) from 0 to 5% by weight of a lipid phase, based on the total weight of the preparations.

27 Claims, No Drawings

COSMETIC OR DERMATOLOGICAL OIL/WATER EMULSIONS WITH REDUCED LIPID CONTENT

This application is a continuation of U.S. application Ser. No. 09/622,090, filed on Feb. 14, 2001 now abandoned, which is, in turn, a 371 of PCT/EP99/00581 filed on Jan. 29, 1999.

The present invention relates to cosmetic and dermatological preparations, in particular those of the oil-in-water type, to processes for their preparation and to their use for cosmetic and medicinal purposes.

The human skin is man's largest organ and performs a number of vital functions. Having an average area of about 2 m$^2$ in adults, it has a prominent role as a protective and sensory organ. The purpose of this organ is to transmit and avert mechanical, thermal, actinic, chemical and biological stimuli. In addition, it has an important role as a regulatory and target organ in human metabolism.

The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes), and also to assist its horny layer in its natural regeneration ability where damage has occurred.

If the barrier properties of the skin are impaired, increased resorption of toxic or allergenic substances or infection by microorganisms may result, leading to toxic or allergic skin reactions.

Another aim of skin care is to compensate for the loss by the skin of sebum and water caused by daily washing. This is particularly important if the natural regeneration ability is inadequate. Furthermore, skin care products should protect against environmental influences, in particular against sun and wind, and delay skin ageing.

Medicinal topical compositions usually comprise one or more medicaments in an effective concentration. For the sake of simplicity, in order to clearly distinguish between cosmetic and medicinal use and corresponding products, reference is made to the legal provisions in the Federal Republic of Germany (e.g. Cosmetics Directive, Foods and Drugs Act).

The term emulsion generally means heterogeneous systems which consist of two liquids which are immiscible or miscible with one another only to a limited extent, which are usually referred to as phases. In an emulsion, one of the two liquids is dispersed in the form of very fine droplets in the other liquid.

If the two liquids are water and oil and oil droplets are very finely dispersed in water, this is an oil-in-water emulsion (O/W emulsion, e.g. milk). The basic character of an O/W emulsion is determined by the water. In the case of a water-in-oil emulsion (W/O emulsion, e.g. butter), the principle is reversed, the basic structure being determined here by the oil.

The person skilled in the art is of course aware of a large number of ways to formulate stable O/W preparations for cosmetic or dermatological use, for example in the form of creams and ointments which can be spread in the range from room temperature to skin temperature, or as lotions and milks, which are more likely flowable in this temperature range.

An object of the present invention was to provide preparations which have a very low lipid content and do not have the disadvantages of the prior art.

Cosmetic gels enjoy immense popularity amongst consumers. Since they are mostly transparent, often coloured or may just as often be colourless and clear, they offer the cosmetics developer additional design opportunities, some of which are functional in character, whilst some are merely used to improve the external appearance. Thus, it is, for example, possible to impart interesting optical effects to the product (which is then usually offered to the observer in transparent packaging), using incorporated colour pigments, gas bubbles and the like, or alternatively, even larger objects.

It is desirable that these objects remain stationary in the gel formulation and do not sink to the bottom or migrate undesirably in any other way in the formulations, especially if it is desired that the incorporated object(s)—be they discernible as such with the naked eye, or be they present in microscopic dimensions, but arranged interestingly—for example in the form of artificially produced coloured swirls—then nevertheless produce visible shapes.

Liquids can be characterized with regard to their rheological properties by their flow and deformation behaviour. As a result of external forces, ideally elastic bodies undergo elastic deformation which spontaneously and completely reverses when the external force is removed. The shape of ideally viscous bodies is changed irreversibly as a result of external forces. The increasing deformation is referred to as flow. Most liquids are neither ideally viscous nor ideally elastic, but show both viscous and elastic properties and are thus referred to as viscoelastic substances.

In the majority of viscoelastic solutions, dispersed particles or gas bubbles will always sink or rise respectively. They have a finite structural relaxation time. This means that the networks in these systems react to a deformation with a corresponding shear stress. However, this will relax to zero in a finite time so that the whole solution reverts to a stable steady state without strain. This also means that these solutions have a defined zero-shear viscosity and thus reach a constant viscosity at low shear rates.

In contrast to these systems, however, there are also those in which dispersed particles or gas bubbles do not sediment. It is noticeable that these systems only flow above a characteristic value. This value is called the flow limit. Closer inspection of the rheological properties of these systems indicates that the storage modulus is independent of the oscillation frequency over the whole frequency range and is always significantly greater than the loss modulus.

By contrast, the complex viscosity does not reach a constant value even at the lowest frequencies, but continues to increase.

Carbopol gels are crosslinked acrylic acid polymers having a large number of carboxyl groups. In dissolved form, these structures bind water. Neutralization of the carboxyl groups leads, as a result of their electrostatic repulsion, to expansion and thus swelling of the polymer chains. In this state the Carbopol gels achieve their typical rheological properties, such as, for example, the establishment of a flow limit. It is a disadvantage that the formulation of the corresponding preparations soon comes up against its limits if a content of surfactants is to be processed.

Surprisingly, these objects are achieved by cosmetic or dermatological preparations comprising (I) one or more surface-active substances chosen from the group
  (Ia) of alkyl glucosides
  (Ib) of the disaccharides esterified with one or more fatty acid residues (II) one or more surface-active substances chosen from the group
- (IIa) of glycerol esters of saturated or unsaturated fatty acids
- (IIb) of glycol esters of saturated or unsaturated fatty acids
- (IIc) of one or more fatty alcohols chosen from the group of branched and unbranched alkyl alcohols having 12 to 40 carbon atoms (III) a water phase (IV) from 0 to 5% by weight of a lipid phase, based on the total weight of the preparations.

It had therefore not been foreseen by the person skilled in the art that the preparations according to the invention
- would be more effective as moisture-donating preparations,
- would be easier to formulate,
- would better promote skin smoothing,
- would be characterized by a better care action,
- would be better vehicles for cosmetic and medicinal-dermatological active ingredients,
- would have better sensory properties, such as, for example, the dispersibility on the skin or absorption into the skin,
- would have higher stability against splitting into oil and water phases, and
- would exhibit better biocompatibility than the preparations of the prior art.

The invention further relates to the use of
(I) one or more surface-active substances chosen from the group
- (Ia) of alkyl glucosides
- (Ib) of the disaccharides esterified with one or more fatty acid residues (II) one or more surface-active substances chosen from the group
- (IIa) of glycerol esters of saturated or unsaturated fatty acids
- (IIb) of glycol esters of saturated or unsaturated fatty acids
- (IIc) of one or more fatty alcohols chosen from the group of branched and unbranched alkyl alcohols having 12 to 40 carbon atoms (III) a water phase (IV) from 0 to 5% by weight of a lipid phase, based on the total weight of the preparations for the preparation of cosmetic or dermatological preparations, in particular of O/W emulsions.

The lipid content of the preparations obtainable according to the invention can advantageously be varied from 0% by weight to 5% by weight, with equally favourable results being achieved. In cases where no lipid is present, the system is not an emulsion, but a system which is most appropriately referred to as an emulsifier gel.

The preparations according to the invention are characterized by a low lipid content or can also be lipid-free.

By using the constituents advantageous according to the invention, it is also possible to formulate gels which are characterized by a light nongreasy feel on the skin, are less sticky, but nevertheless exhibit good skincare performance. Small amounts (<5%) of various common lipids can be added to these gels and, as a result, their sensory properties can be subtly differentiated.

Preferably, preparations according to the invention comprise up to 3% by weight of a lipid phase and are then O/W emulsions. Preparations according to the invention particularly advantageously comprise up to 2.5% by weight of a lipid phase, in each case based on the total weight of the preparation.

The alkyl glucosides are preferably chosen from the group of alkyl glucosides characterized by th structural formula

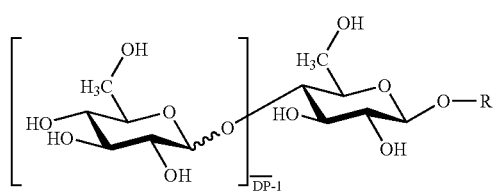

where R is a branched or unbranched alkyl radical having 4 to 24 carbon atoms, and where $\overline{DP}$ is an average degree of glucosylation of up to 2.

R is advantageously chosen from the group of unbranched alkyl radicals, the myristyl radical, the cetyl radical, the stearyl radical, the eicosyl radical, the arachidyl radical and the behenyl radical being preferred.

Alkyl glucosides used according to the invention are obtainable by processes as described, for example, in DE-A 40 40 655 and other specifications. They are available commercially from various manufacturers.

Alkyl glucosides which are covered by the invention are, for example, Emulgade PL 68/50 (Henkel), Tego Care SG 90 (Goldschmidt), Montanov 68 (Seppic) comprising cetylstearyl glucoside+cetylstearyl alcohol, Montanov 202 (Seppic) cetylstearyl alcohol+cocoyl glucoside, Montanov 202 (Seppic) arachidyl glucoside+arachidyl alcohol+behenyl alcohol.

It is, for example, advantageous to use mixtures of stearyl glucoside and cetyl glucoside. Such mixtures are commercially available, for example under the trade name Tego® Care SG 90 from Th.Goldschmidt KG.

The total amount of one or more alkyl glucosides used according to the invention in the finished cosmetic or dermatological preparations is advantageously chosen from the range 0.1–10.0% by weight, preferably 0.5–6.0% by weight, based on the total w ight of the preparation.

Preferred sugar esters according to the invention are esters of fatty acids and sucrose, monoesterified or completely esterified, and commercially available cosmetic for materials comprising the same.

Sucrose has the following characteristic structure:

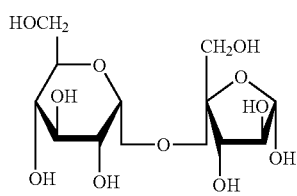

Its esters, which can advantageously be used according to the invention, are characterized by the structure

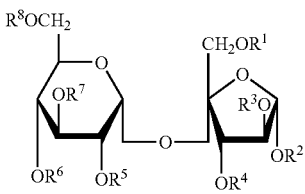

where $R^1$–$R^8$, advantageously independently of one another, can be chosen from the group of hydrogen atoms and branched and unbranched alkanoyl groups having 1–24 carbon atoms. In particular, it is advantageous if up to seven of the radicals $R^1$–$R^8$ are hydrogen atoms and one to eight of the radicals $R^1$–$R^8$ are chosen from the group of branched and unbranched alkanoyl groups having 8–20 carbon atoms, of these, in particular, the lauroyl radical and the myristoyl radical.

Sugar esters of sucrose and fatty acids are, for example, obtainable from Grillo Cosmetics [e.g. Grilloten LSE 65 K (ester of sucrose and coconut fatty acids), Grilloten LSE 65 K soft (ester of sucrose and coconut fatty acids), Grilloten LSE 87 K (ester of sucrose and coconut fatty acids), Grilloten LSE 87 K soft (ester of sucrose and coconut fatty acids) or Grilloten PSE 141 G (ester of sucrose and palmitic acid/stearic acid)], Stéarinerie Dubois [e.g. Distéarate de Saccharose (sucrose distearate), Palmitate de Saccharose (sucrose palmitate)], Sist rna [e.g. Sisterna SP 70 C (sucrose palmitate/stearate), Sisterna SP 50 C (sucrose palmitate/stearate), Sisterna SP 30 C (sucrose palmitate/stearate), Sisterna SP 10 C (sucrose palmitate/stearate), Sist ma SP 01 C (sucrose distearate) or Sisterna L 70 C (sucrose laurate)], and Mitsubishi Kagaku Foods Corporation [e.g. Ryoto Sugar Ester L 1695 (sucrose laurate), Ryoto Sugar Ester M 1695 (sucrose myristate), Ryoto Sugar Ester M 595 (mixture of sucrose mono-, di- and trimyristate), Ryoto Sugar Ester P 1570 (sucrose palmitate), Ryoto Sugar Ester S-570 (sucrose distearate), Ryoto Sugar Ester S-370 (sucrose tristearate), Ryoto Sugar Ester S-270 (sucrose tetrastearate), Ryoto Sugar Ester S-170 (sucrose pentastearate), Ryoto Sugar Ester S-1170 (mixture of sucrose mono-, di- and tristearate)].

The total amount of one or more sucrose esters used according to the invention in the finished cosmetic or dermatological preparations is advantageously chosen from the range 0.1–10.0% by weight, preferably 0.5–6.0% by weight, based on the total weight of the preparations.

The glycerol esters of saturated or unsaturated fatty acids can advantageously be chosen from the group of glyceryl monoesters of monobasic fatty acids having, on average, 8–30 carbon atoms. It is particularly advantageous to use glycerol esters which are chosen either from the group of glycerol esters of wool wax acids or from the group of glycerol esters of palmitic or stearic acid.

Glycerol esters of wool wax acids and their use as W/O emulsifiers are known per se. German Patent Specification 20 23 786 describe such glycerol esters, their preparation and their use. There are a large number of cosmetic and dermatological products, including sunscreen products, with a content of such glycerol esters as emulsifiers or coemulsifiers.

Wool wax or wool grease is the term for the grease-like to wax-like constituent of raw sheep's wool produced during the scouring of raw wool. The wool wax consists of a mixture of fatty acid esters of higher alcohols and of free fatty acids. The main constituents of the wool wax acids are (a) saturated unsubstituted carboxylic acids according to the formula

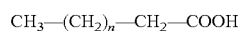

(b) α-hydroxycarboxylic acids according to the formula

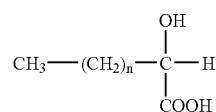

(c) ω-hydroxycarboxylic acids according to the formula

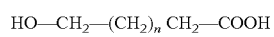

(d) isocarboxylic acids according to the formula

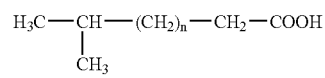

(e) α-hydroxyisocarboxylic acids according to the formula

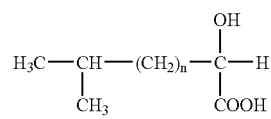

(f) ω-hydroxyisocarboxylic acids according to the formula

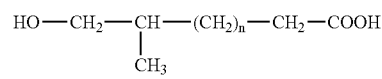

(g) anteisocarboxylic acids according to the formula

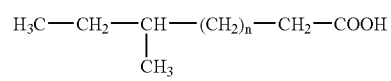

(h) α-hydroxyanteisocarboxylic acid according to the formula

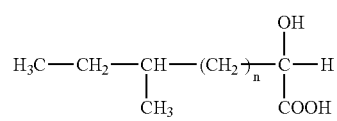

(i) ω-hydroxyanteisocarboxylic acids according to the formula

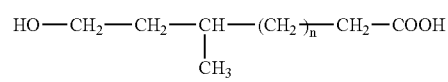

Here, n usually assumes values from 7-31. Representative compositions of the wool wax acids are described, for example in "Parfümerie und Kosmetik" [Perfumery and Cosmetics], 59th annual edition, No. 12/78, p.429, 430 and in the "Lexikon der Hilfsstoffe für Pharmazie, Kosmetik und angrenzende Gebiete" [Lexicon of auxiliaries for pharmacy, cosmetics and related fields] by H. P. Fiedler, 1989, 3rd edition, Editio Cantor Aulendorf.

Raw wool wax acids are not usually suitable for cosmetic purposes, instead distilled wool wax acids are normally used. This fact and corresponding processes for the refinement of raw wool wax acids are known to the person skilled in the art.

Wool wax acids typically consist of about 60% of saturated unsubstituted carboxylic acids, about 30% of α-hydroxycarboxylic acids and about 5% of ω-hydroxycarboxylic acids, the remainder being made up of about 5% of essentially the other above-mentioned types of carboxylic acid.

The total amount of one or more glycerol esters used according to the invention in the finished cosmetic or dermatological preparations is advantageously chosen from the range 0.1-10.0% by weight, preferably 0.5-6.0% by weight, based on the total weight of the preparations.

The glycol ester or glycol esters of saturated or unsaturated fatty acids can advantageously be chosen from the group of glycol monoesters of monobasic fatty acids having, on average, 8-30 carbon atoms. It is particularly advantageous to use glycol esters chosen from the group of glycol esters of palmitic or stearic acid.

The preferred fatty alcohol used according to the invention is cetylstearyl alcohol (a mixture of 1-hexadecanol and 1-octadecanol in equal amounts).

The total amount of one or more fatty alcohols used according to the invention in the finished cosmetic or dermatological preparations is advantageously chosen from the range 0.1-10.0% by weight, preferably 0.5-6.0% by weight, based on the total weight of the preparations.

According to the invention, it is advantageous to choose weight ratios of one or more partially neutralized esters of monoglycerides and/or diglycerides of saturated fatty acids with citric acid on the one hand and fatty alcohols on the other hand of from 10:1 to 1:5, preferably from 6:1 to 1:1, particularly preferably of about 3:1.

The weight ratio of the total of the constituents of one or more partially neutralized esters of monoglycerides and/or diglycerides of saturated fatty acids with citric acid, and fatty alcohols to the oil phase is chosen according to the invention from the range from 20:1 to 1:5, advantageously from the range from 20:1 to 1:2, particularly preferably about 1:1.

The oil phase of the O/W emulsions according to the invention is advantageously chosen from the group of lecithins and of fatty acid triglycerides, namely the triglycerol esters of saturated and/or unsaturated, branched and/or unbranched alkanecarboxylic acids having a chain length of from 8 to 24 carbon atoms, in particular 12 to 18 carbon atoms. The fatty acid triglycerides can, for example, be advantageously chosen from the group of synthetic, semisynthetic and natural oils, such as, for example, olive oil, sunflower oil, soya oil, peanut oil, rapeseed oil, almond oil, palm oil, coconut oil, castor oil, wheatgerm oil, grapeseed oil, thistle oil, evening primrose oil and the like.

The oils according to the invention are likewise advantageously chosen from the group consisting of Vaseline (petrolatum), paraffin oil and polyolefins. Of the polyolefins, polydecenes are the preferred substances.

For the purposes of the present invention, the oil phase can additionally advantageously be chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, and from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, such as, for example, jojoba oil.

The oil phase can also advantageously be chosen from the group of branched and unbranched hydrocarbons and hydrocarbon waxes, silicone oils, dialkyl ethers, and the group of saturated or unsaturated, branched or unbranched alcohols.

Any desired mixtures of such oil and wax components can also be used advantageously for the purposes of the present invention. In some cases, it may also be advantageous to use waxes, for example cetyl palmitate, as the sole lipid component of the oil phase.

Of the hydrocarbons, paraffin oil, squalane and squalene are used advantageously for the purposes of the present invention.

The oil phase can advantageously also have a content of cyclic or linear silicone oils or consist entirely of such oils, although it is preferable to use an additional content of other oil phase components apart from the silicone oil or the silicone oils.

Cyclomethicone (octamethylcyclotetrasiloxane) is advantageously used as the silicone oil to be used according to the invention. However, other silicone oils can also be used advantageously for the purposes of the present invention, for example hexamethylcyclotrisiloxane, polydimethylsiloxane and poly(methylphenylsiloxane).

The aqueous phase of the preparations according to the invention in some instances advantageously comprises alcohols, diols or polyols of low carbon number, and ethers thereof, preferably ethanol, isopropanol, propylene glycol, glycerol, ethylene glycol, ethylene glycol monoethyl ether or monobutyl ether, propylene glycol monomethyl, monoethyl or monobutyl ethers, diethylene glycol monomethyl or monoethyl ethers and analogous products, and also alcohols of low carbon number, e.g. ethanol, isopropanol, 1,2-propanediol, glycerol and, in particular, one or more thickeners which can advantageously be chosen from the group consisting of silicon dioxide, aluminium silicates, polysaccharides or derivatives thereof, e.g. hyaluronic acid, xanthan gum, hydroxypropylmethylcellulose.

Particularly advantageously, the preparations according to the invention are also gel-like preparations. For this reason, thickeners based on acrylate/alkyl acrylate copolymers have proven advantageous. In particular, these thickeners are advantageously chosen from the group of carbomers or Carbopols (Carbopol®: actually a registered trade mark of BFGoodrich Company). In particular, the acrylate/alkyl acrylate copolymer or copolymers to be used advantageously according to the invention are characterized by a structure as follows:

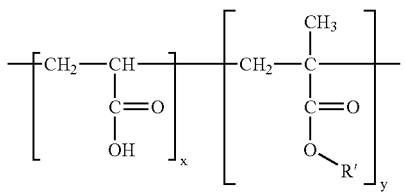

Here, R' is a long-chain alkyl radical, x and y are numbers which symbolize the respective stoichiometric proportion of the comonomers in each case.

Examples of acrylate/alkyl acrylate copolymers which can be used advantageously are products such as Carbopol® 1382 from BFGoodrich Company, but also Carbopol grades 980, 981, 1382, 2984, 5984, but also ETD (Easy-to-disperse) grades 2001, 2020, 2050, in each case individually or in any combinations with one another.

The total amount of one or more of surface-active acrylate/alkyl acrylate copolymers used advantageously according to the invention in the finished cosmetic or dermatological preparations is advantageously chosen from the range 0.1–10.0% by weight, preferably 0.5–2.5% by weight, based on the total weight of the preparation.

Particularly advantageous preparations are also obtained when antioxidants are used as additives or active ingredients. According to the invention, the preparations advantageously comprise one or more antioxidants. Antioxidants which are favourable but which are nevertheless optional may be all antioxidants which are customary or suitable for cosmetic and/or dermatological applications.

The antioxidants are advantageously selected from the group consisting of amino acids (e.g. glycine, histidine, tyrosine, tryptophan) and derivatives thereof, imidazoles, (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, ψ-lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, ferulic acid and derivatives thereof, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide), and the derivatives (salts, esters, ethers, sugars, nucleotides, nucleosides, peptides and lipids) of said active substances which are suitable according to the invention.

For the purposes of the present invention, water-soluble and also oil-soluble antioxidants can be used particularly advantageously.

A surprising property of the present invention is that preparations according to the invention are very good vehicles for cosmetic or dermatological active ingredients into the skin, preferred active ingredients being antioxidants which are able to protect the skin against oxidative stress. Preferred antioxidants are vitamin E and derivatives thereof and vitamin A and derivatives thereof.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof are used as the antioxidant or antioxidants, the respective concentrations thereof are advantageously chosen from the range 0.001–10% by weight, based on the total weight of the formulation.

If vitamin A or vitamin A derivatives or carotenes or derivatives thereof are used as the antioxidant or antioxidants, the respective concentrations thereof are advantageously chosen from the range 0.001–10% by weight, based on the total weight of the formulation.

The person skilled in the art is of course aware that cosmetic preparations are in most cases inconceivable without the customary auxiliaries and additives. The cosmetic and dermatological preparations according to the invention can, accordingly, also comprise cosmetic auxiliaries, as are customarily used in such preparations, for example bodying agents, stabilizers, fillers, preservatives, perfumes, antifoams, dyes, pigments which have a colouring action, thickeners, surface-active substances, emulsifiers, emollients, moisturizers and/or humectants, anti-inflammatory substances, additional active ingredients such as vitamins or proteins, sunscreens, insect repellents, bactericides, virucides, water, salts, antimicrobial, proteolytic or keratolytic substances, medicaments or other customary constituents of a cosmetic or dermatological formulation such as alcohols, polyols, polymers, foam stabilizers, organic solvents or also electrolytes.

The latter can be chosen, for example, from the group of salts containing the following anions: chlorides, also inorganic oxo element anions, of these, in particular sulphates, carbonates, phosphates, borates and aluminates. Electrolytes based on organic anions are also advantageous, e.g. lactates, acetates, benzoates, propionates, tartrates, citrates, amino acids, ethylenediaminetetraacetic acid and salts thereof and others. Preferred cations of the salts are ammonium, alkylammonium, alkali metal, alkaline earth metal, magnesium, iron or zinc ions. It does not need to be mentioned that only physiologically acceptable electrolytes should be used in cosmetics. Particular preference is given to potassium chloride, sodium chloride, magnesium sulphate, zinc sulphate and mixtures thereof.

Corresponding requirements apply mutatis mutandis to the formulation of medicinal preparations.

The preparations according to the invention, in particular O/W emulsions, can be used as a basis for cosmetic or dermatological formulations. The latter can have the customary composition and be used, for example, for the treatment and care of the skin and/or the hair, as lip care product, as deodorant product and as make-up or make-up remover product in decorative cosmetics or as a sunscreen preparation. For use, the cosmetic and dermatological preparations according to the invention are applied to the skin and/or the hair in a sufficient amount in a manner customary for cosmetics or dermatological compositions.

For the purposes of the present invention, cosmetic or topical dermatological compositions can accordingly, depending on their composition, be used, for example, as a skin protection cream, cleansing milk, sunscreen lotion, nourishing cream, day or night cream, etc. In some circumstances it is possible and advantageous to use the compositions according to the invention as a base for pharmaceutical formulations.

The low-viscosity cosmetic or dermatological compositions according to the invention can, for example, be in the form of preparations which can be sprayed from aerosol containers, squeezable bottles or by means of a pump device, or in the form of a liquid composition which can be applied by means of roll-on devices, but also in the form of an emulsion which can be applied from standard bottles and containers.

Suitable propellants for cosmetic or dermatological preparations which can be sprayed from aerosol containers for the purposes of the present invention are the customary known readily volatile, liquefied propellants, for example hydrocarbons (propane, butane, isobutane), which can be used alone or in a mixture with one another. Compressed air is also used advantageously.

The person skilled in the art is of course aware that there are propellants which are non-toxic per se which would be suitable in principle for realizing the present invention in the form of aerosol preparations, but which must nevertheless be avoided because of their unacceptable impact on the environment or other accompanying circumstances, in particular fluorinated hydrocarbons and chlorofluorocarbons (CFCs).

Favourable cosmetic and dermatological preparations are also those in the form of a sunscreen. As well as the active ingredient combinations according to the invention, these preferably additionally comprise at least one UV-A filter substance and/or at least one UV-B filter substance and/or at least one inorganic pigment.

For the purposes of the present invention, however, it is also advantageous to provide cosmetic and dermatological preparations whose main purpose is not protection against sunlight, but which nevertheless have a content of UV protectants. Thus, for example, UV-A or UV-B filter substances are usually incorporated into day creams.

UV protectants, like antioxidants and, if desired, preservatives, also effectively protect the preparations themselves against spoilage.

Preparations according to the invention can furthermore advantageously comprise substances which absorb UV radiation in the UV-B range, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the entire region of ultraviolet radiation. They can also be used as sunscreens for the hair or the skin.

If the emulsions according to the invention contain UV-B filter substances, the latter may be oil-soluble or water-soluble. Examples of oil-soluble UV-B filters which are advantageous according to the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethyl-amino)benzoate, amyl 4-(dimethylamino) benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxybenzalmalonate;

derivatives of 1,3,5-triazine, preferably 2,4,6-trianilino(p-carbo-2'-ethyl-1'-hexyloxy)-1,3,5-triazine.

The list of said UV-B filters, which may be used in combination with the active ingredient combinations according to the invention is of course not intended to be limiting.

It can also be advantageous to formulate lipodispersions according to the invention with UV-A filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)-propane-1,3-dione.

Cosmetic and dermatological preparations according to the invention can also comprise inorganic pigments which are customarily used in cosmetics for protecting the skin against UV rays. These are oxides of titanium, zinc, iron, zirconium, silicon, manganese, aluminium, cerium and mixtures thereof, and modifications in which the oxides are the active agents. Particular preference is given to pigments based on titanium dioxide.

Further constituents which can be used are:

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alcohols, diols or polyols of low carbon number, and ethers thereof, preferably ethanol, isopropanol, propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products.

The examples below serve to illustrate the present invention without limiting it. The numerical values in the examples refer to percentages by weight, based on the total weight of the respective preparations.

EXAMPLE 1

|  |  | % by weight |
|---|---|---|
| Sucrose palmitate/stearate (Sisterna SP-30 C) |  | 6.00 |
| Glycerol |  | 3.00 |
| Preservative |  | q.s. |
| Water | ad | 100.00 |

EXAMPLE 2

|  |  | % by weight |
|---|---|---|
| Sucrose tetrastearate (Sucrose Ester S-270) |  | 2.00 |
| Cetearyl alcohol |  | 4.00 |
| Glycerol |  | 3.00 |
| Preservative |  | q.s. |
| Water | ad | 100.00 |

EXAMPLE 3

|  |  | % by weight |
|---|---|---|
| Sucrose laurate (Sisterna SP 70-C) |  | 3.00 |
| Stearyl alcohol |  | 3.00 |
| Glycerol |  | 3.00 |
| Panthenol |  | 0.50 |
| Preservative |  | q.s. |
| Water | ad | 100.00 |

EXAMPLE 4

|  |  | % by weight |
|---|---|---|
| Stearyl glucoside and cetyl glucoside (Emulgade PL 68/50) |  | 4.00 |
| Glycerol |  | 3.00 |
| Allantoin |  | 0.30 |
| Bisabolol |  | 0.50 |
| Carbomer |  | 0.20 |
| NaOH 45% strength |  | 0.10 |
| Preservative |  | q.s. |
| Water | ad | 100.00 |

EXAMPLE 5

|  |  | % by weight |
|---|---|---|
| Stearyl glucoside and cetyl glucoside (Tego Care SG 90) |  | 2.00 |
| Glycerol |  | 3.00 |
| Squalane |  | 3.00 |
| Carbomer |  | 0.60 |
| NaOH 45% strength |  | 0.30 |
| Preservative |  | q.s. |
| Water | ad | 100.00 |

EXAMPLE 6

|  |  | % by weight |
|---|---|---|
| Arachidyl glucoside + arychidyl alcohol + behenyl alcohol (Montanov 202) |  | 6.00 |
| Glycerol |  | 3.00 |
| Mineral oil |  | 1.00 |
| Isopropyl palmitate |  | 1.00 |
| Cyclomethicone |  | 1.00 |
| Carbomer |  | 0.20 |
| NaOH 45% strength |  | 0.10 |
| Preservative |  | q.s. |
| Water | ad | 100.00 |

EXAMPLE 7

|  |  | % by weight |
|---|---|---|
| Sucrose palmitate/stearate (Sisterna SP 70-C) |  | 2.00 |
| Glyceryl lanolate |  | 2.00 |
| Glycerol |  | 3.00 |
| Dimethicone |  | 2.00 |
| Liquorice root extract |  | 2.00 |
| Carbomer |  | 0.20 |
| NaOH 45% strength |  | 0.10 |
| Preservative |  | q.s. |
| Water | ad | 100.00 |

EXAMPLE 8

|  |  | % by weight |
|---|---|---|
| Sucrose tetrastearate (Sucrose Ester S-270) |  | 1.00 |
| Glyceryl stearate |  | 3.00 |
| Glycerol |  | 3.00 |
| Dimethicone |  | 1.00 |
| Mineral oil |  | 3.00 |
| Carbomer |  | 0.40 |
| NaOH 45% strength |  | 0.20 |
| Preservative |  | q.s. |
| Water | ad | 100.00 |

EXAMPLE 9

|  | % by weight |
| --- | --- |
| Decyl glucoside | 1.00 |
| Glyceryl lanolate | 1.50 |
| Dimethicone copolyol | 2.00 |
| Triceteareth-4-phosphate | 0.70 |
| Isopropyl palmitate | 1.00 |
| Carbomer | 0.60 |
| NaOH 45% strength | 0.30 |
| Preservative | q.s. |
| Water ad | 100.00 |

EXAMPLE 10

|  | % by weight |
| --- | --- |
| Ester of sucrose and palmitic acid/stearic acid (Grilloten PSE 141 G) | 1.00 |
| Glycol stearate | 3.00 |
| Panthenol | 3.00 |
| Dimethicone | 1.00 |
| Jojoba oil | 2.00 |
| Carbomer | 0.40 |
| NaOH 45% strength | 0.20 |
| Preservative | q.s. |
| Water ad | 100.00 |

The invention claimed is:

1. A cosmetic or dermatological preparation comprising
   (I) one or more surface-active substances selected from disaccharides which are esterified with one or more fatty acid residues;
   (II) one or more surface-active substances selected from
      (IIa) glycerol esters of saturated or unsaturated fatty acids;
      (IIb) glycol esters of saturated or unsaturated fatty acids; and
      (IIc) branched and unbranched alkyl alcohols having from 12 to 40 carbon atoms;
   (III) a water phase; and
   (IV) from 0 to 5% by weight of a lipid phase, based on a total weight of the preparation.

2. The preparation of claim 1, wherein the preparation comprises from 0 to 3% by weight of the lipid phase.

3. The preparation of claim 1, wherein the preparation does not comprise a lipid phase.

4. The preparation of claim 1, wherein (I) comprises disaccharides which are esterified with one to four fatty acid residues.

5. The preparation of claim 1, wherein (I) comprises a sucrose ester.

6. The preparation of claim 1, wherein (I) comprises sucrose which is esterified with one or more alkanecarboxylic acids having from 8 to 20 carbon atoms.

7. The preparation of claim 6, wherein the sucrose is esterified with at least one of lauric acid and myristic acid.

8. The preparation of claim 1, wherein (IIa) comprises glyceryl monoesters of monobasic fatty acids having from 8 to 30 carbon atoms on the average.

9. The preparation of claim 1, wherein (IIb) comprises glycol monoesters of monobasic fatty acids having from 8 to 30 carbon atoms on the average.

10. The preparation of claim 1, wherein (IIc) comprises cetylstearyl alcohol.

11. The preparation of claim 1, wherein the preparation further comprises one or more acrylate/alkyl acrylate copolymers.

12. A cosmetic or dermatological preparation comprising
    (I) one or more surface-active substances selected from
       (Ia) alkyl glucosides; and
       (Ib) disaccharides which are esterified with one or more fatty acids; and
    (II) one or more surface-active substances selected from
       (IIa) glycerol esters of saturated or unsaturated fatty acids; and
       (IIb) glycol esters of saturated or unsaturated fatty acids;
    (III) a water phase; and
    (IV) from 0 to 5% by weight of a lipid phase, based on a total weight of the preparation.

13. The preparation of claim 12, wherein the preparation comprises from 0 to 3% by weight of the lipid phase.

14. The preparation of claim 12, wherein the preparation does not comprise a lipid phase.

15. The preparation of claim 12, wherein (IIa) comprises glyceryl monoesters of monobasic fatty acids having from 8 to 30 carbon atoms on the average.

16. The preparation of claim 12, wherein (IIb) comprises glycol monoesters of monobasic fatty acids having from 8 to 30 carbon atoms on the average.

17. The preparation of claim 12, wherein (Ia) comprises compounds of formula

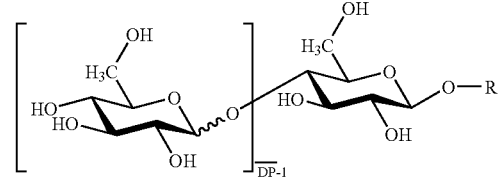

wherein R is a branched or unbranched alkyl radical having from 4 to 24 carbon atoms and DP represents an average degree of glucosylation of up to 2.

18. The preparation of claim 17, wherein R comprises at least one of myristyl, cetyl, stearyl, eicosyl, arachidyl and behenyl radicals.

19. The preparation of claim 12, wherein the preparation further comprises one or more acrylate/alkyl acrylate copolymers.

20. A cosmetic or dermatological preparation comprising
    (I) one or more surface-active substances selected from
       (Ia) alkyl glucosides of formula

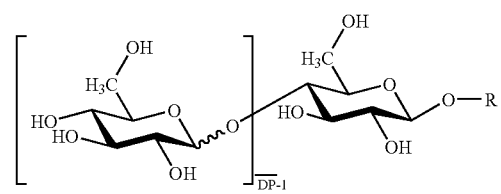

wherein R comprises at least one of myristyl, cetyl, stearyl, elcosyl, arachidyl and behenyl radicals and DP represents an average degree of glucosylation of up to 2; and (Ib) disaccharides which are esterified with one or more fatty acid residues; and
(II) one or more surface-active substances selected from
(IIa) glycerol esters of saturated or unsaturated fatty acids;
(IIb) glycol esters of saturated or unsaturated fatty acids; and
(IIc) branched and unbranched alkyl alcohols having from 12 to 40 carbon atoms;
(III) a water phase;
(IV) from 0 to 3% by weight of a lipid phase, based on a total weight of the preparation; and
(V) one or more acrylate/alkyl acrylate copolymers.

21. The preparation of claim 20, wherein the preparation does not comprise a lipid phase.

22. The preparation of claim 20, wherein (IIa) comprises glyceryl monoesters of monobasic fatty acids having from 8 to 30 carbon atoms on the average.

23. The preparation of claim 20, wherein (IIb) comprises glycol monoesters of monobasic fatty acids having from 8 to 30 carbon atoms on the average.

24. The preparation of claim 20, wherein (IIc) comprises cetylstearyl alcohol.

25. A method of caring for skin, wherein the method comprises applying to skin the preparation of claim 1.

26. A method of caring for skin, wherein the method comprises applying to skin the preparation of claim 12.

27. A method of caring for skin, wherein the method comprises applying to skin the preparation of claim 20.

* * * * *